United States Patent [19]

Neukam et al.

[11] Patent Number: 4,522,764
[45] Date of Patent: Jun. 11, 1985

[54] PROCESS FOR THE PRODUCTION OF α, β-UNSATURATED CARBOXYLIC ACID ALKYL ESTERS SULFONATED IN THE α-POSITION AND COMPOUNDS OBTAINABLE BY THIS PROCESS

[75] Inventors: Theo Neukam, Dormagen; Wolfgang Bräuer; Siegfried Korte, both of Leverkusen, all of Fed. Rep. of Germany

[73] Assignee: Bayer Aktiengesellschaft, Leverkusen, Fed. Rep. of Germany

[21] Appl. No.: 517,483

[22] Filed: Jul. 26, 1983

Related U.S. Application Data

[62] Division of Ser. No. 396,567, Jul. 9, 1982, abandoned.

[30] Foreign Application Priority Data

Jul. 29, 1981 [DE] Fed. Rep. of Germany ....... 3129980

[51] Int. Cl.³ ............................................ C07C 143/68
[52] U.S. Cl. .................. 260/456 R; 560/149
[58] Field of Search .................... 560/149; 260/513 T, 260/456 R

[56] References Cited

U.S. PATENT DOCUMENTS 2,743,288  4/1956  Rueggeberg et al. .......... 260/513 T

FOREIGN PATENT DOCUMENTS 2110792  5/1972  France .

OTHER PUBLICATIONS

Berre et al., Bulletin de la Societe Chimique de France 1973, No. 7–8, pp. 2266–2269.
Backer et al., Quelques Acides α-Sulfocarboxyliques Non Satures Simples, Par H. J. Backer et R. D. Mulder, 547.391–868, Rec. Trav. Chim. 62, 46–52 (1943).

*Primary Examiner*—Nicky Chan
*Attorney, Agent, or Firm*—Sprung, Horn, Kramer & Woods

[57] ABSTRACT

The title compounds are obtained by reacting compounds corresponding to the following formula:

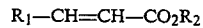

$$R_1—CH=CH—CO_2R_2$$

wherein $R_1$ represents hydrogen or a methyl group and $R_2$ represents a primary or secondary $C_1$ to $C_4$ alkyl group, with from 0.6 to 1.6 mol. equivalents of $SO_3$ and, optionally, with from 0.1 to 10 mol. equivalents of an alkylating agent at temperatures in the range from $-10°$ to $+25°$ C., subsequently heating the resulting reaction mixture for 0.5 to 6 hours to $70°–200°$ C. and then working it up by distillation.

7 Claims, No Drawings

PROCESS FOR THE PRODUCTION OF α, β-UNSATURATED CARBOXYLIC ACID ALKYL ESTERS SULFONATED IN THE α-POSITION AND COMPOUNDS OBTAINABLE BY THIS PROCESS

This is a division of application Ser. No. 396,567, filed July 9, 1982, now abandoned.

This invention relates to a process for the production of sulfonated α,β-unsaturated carboxylic acid alkyl esters corresponding to the following general formula (I):

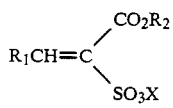

in which
$R_1$ represents a hydrogen atom or a methyl group,
$R_2$ represents a primary or secondary alkyl group containing from 1 to 4 carbon atoms and
X represents a hydrogen atom or a primary or secondary alkyl group containing from 1 to 4 carbon atoms, and to their sulfonic acid salts.

The present invention also relates to compounds corresponding to the following formula (I)

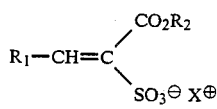

in which $R_1$ and $R_2$ are as previously defined and $X^\oplus$ represents a proton or a metal ion equivalent, preferred metals being alkali metal and alkaline earth metals, zinc and aluminium.

It is already known that α,β-unsaturated carboxylic acids can be converted into sulfonic acid derivatives by reaction with sulfonation reagents (Rec. Trav. Chim. 62, 46 (1943); U.S. Pat. No. 2,895,987; FR-PS No. 2,110,792, Bull. Soc. Chim. Fr. 1973, 2266). However, the 2-sulfoacrylic acid has only ever been produced in dilute solution because it polymerises when the solution is concentrated.

Attempts to isolate the 2-sulfoacrylic acid by sulfonation with pure sulfur trioxide were also unsuccessful.

It is also known that the 3-chloro-2-sulfopropionic acid obtained from acrylic acid by sulfonation with chlorosulfonic acid gives 2-methoxy sulfonyl propenoic acid methyl ester by reaction with chloromethyl formate for 18 hours at 95° C. (FR-PS No. 2,110,792). The highly hygroscopic, dimethyl lauryl ammonium salt of 2-sulfopropenoic acid methyl ester is obtained from 3-chloro-2-sulfopropionic acid by esterification with methanol, reaction with pyridine to form the pyridinium salt and subsequent elimination by dimethyl lauryl amine (Bull. Soc. Chim. Fr. 1973, 2266). One of the disadvantages of these known processes is that the ester derivatives derived from the carboxylic acids and/or sulfonic acids, which are of particular commercial interest, can only be obtained—if at all—by elaborate multi-stage syntheses. These complicated processes cannot be worked on a commercial scale.

A process for the production of compounds corresponding to formula (I) has now been found and is characterised in that α,β-unsaturated carboxylic acid esters corresponding to the following general formula (II):

$$R_1CH=CH-CO_2R_2 \qquad (II)$$

in which $R_1$ and $R_2$ are as previously defined above, are reacted with from 0.6 to 1.6 mol. equivalents of sulfur trioxide and, optionally, with from 0.1 to 10 mol. equivalents of an alkylating agent, based in each case on the unsaturated ester, at temperatures in the range from −10° C. to +25° C., the reaction mixture is heated for 0.5 to 6 hours to temperatures in the range from 70° C. to 200° C. and then worked up by distillation, after which the components of the distillate are optionally separated. Working up by distillation, optionally after the separation of readily volatile constituents, for example unreacted alkylating agent, is carried out in particular by continuously distilling the reaction mixture in a tubular evaporator at temperatures in the range from 100° C. to 250° C. under a pressure of from 0.05 to 30 mbars, the throughput amounting to between 0.1 and 10 kg/m².h. The distillate, which predominantly consists of 5 to 90% by weight of the sulfonic acid (I) (X=H) and 10 to 95% by weight of the sulfonic acid ester (I) (X=$R_2$), is separated by precipitating the sulfonic acid with an organic precipitant or by salt formation. The residual sulfonic acid ester is isolated by distillation.

The α,β-unsaturated carboxylic acid alkyl esters used are, for example, acrylic acid methyl ester, acrylic acid ethyl ester, acrylic acid propyl ester, acrylic acid isopropyl ester, acrylic acid butyl ester, acrylic acid isobutyl ester, crotonic acid methyl ester, crotonic acid ethyl ester, crotonic acid propyl ester, crotonic acid isopropyl ester, crotonic acid butyl ester and crotonic acid isobutyl ester. It is preferred to use acrylic acid methyl ester, acrylic acid ethyl ester and crotonic acid methyl ester.

The α,β-unsaturated carboxylic acid alkyl ester is preferably reacted with from 0.8 to 1.2 mol. equivalents of sulfur trioxide which may be introduced while stirring either in gaseous or liquid form. The sulfur trioxide should be introduced as quickly as possible. However, it is important to ensure that the above-mentioned reaction temperature, preferably in the range from 0° to +10° C., is maintained. Accordingly, the addition time depends upon the size and cooling capacity of the batch. In general, addition of the $SO_3$ takes from 0.1 to 2.0 hours. In the case of highly exothermic reactions, for example where crotonic acid methyl ester is used, it may be advisable to carry out the reaction in the presence of an organic solvent, particularly a low-boiling chlorinated hydrocarbon, such as chloroform or methylene chloride, which is added in a quantity of up to 100% by weight, based on the carboxylic acid ester and sulfur trioxide used. In general, particularly where acrylic acid methyl ester is used, the sulfur trioxide is added in the absence of a solvent.

Suitable alkylating agents are, for example, $C_1$-$C_4$-dialkyl sulfates, alkyl- and aryl alkyl ethers, alcohols, alkyl halides and diazomethane. Dimethyl sulfate is preferred, particularly where acrylic acid methyl ester is the α,β-unsaturated carboxylic acid ester.

It is preferred to use from 0.2 to 5 mol. equivalents of $C_1$-$C_4$-alkyl sulfate, based on the unsaturated ester.

The reaction is normally carried out in batches in a stirrer-equipped reaction, although it may also be carried out continuously in a reaction tube into which the reaction components are simultaneously introduced.

The alkylating agent is added after or during the reaction with sulfur trioxide. Thereafter the reaction mixture is preferably heated for from 1.5 to 3 hours to between 80° and 160° C.

The continuous distillation process may be carried out in a tubular evaporator. It is preferred to use a thin-layer evaporator comprising a rotating wiper or a falling-film evaporator. In this continous distillation process, the temperature is preferably maintained in the range from 140° C. to 200° C. and the pressure preferably maintained in the range from 0.3 to 3 mbar. The residence time in the evaporator amounts to between 0.1 and 10 kg of product per square meter of exchange surface of the tubular evaporator per hour.

The reaction mixture accumulating consists predominantly of the sulfonic acid and the sulfonic acid ester of formula (I). Where the reaction is carried out in the absence of an alkylating agent, the sulfonic acid is predominant. Where the reaction is carried out in the presence of an alkylating agent, it is the sulfonic acid ester which predominates.

The yield of the reaction mixture, based on the quantity of the starting components used, amounts to between 50 and 100% by weight.

The precipitant used for isolating the sulfonic acid of formula (I), in which X represents a hydrogen atom, from the mixture is an organic solvent, preferably an aromatic hydrocarbon, for example benzene, toluene or xylene. A particularly good purifying effect is obtained by briefly heating the mixture with the precipitant, followed by cooling, resulting in precipitation of the sulfonic acid.

The filtrate which is left after separation of the sulfonic acid and which mainly contains the organic solvent and the sulfonic acid ester is freed from the organic solvent by distillation. Subsequent fractional distillation in a column at a temperature of from 70° C. to 200° C. and preferably at a temperature of from 80° C. to 150° C. under a pressure of from 0.05 to 40 mbar and preferably under a pressure of from 0.3 to 7 mbar gives the sulfonic acid ester corresponding to formula (I) in which X=$R_2$.

Another possible method of separating off the sulfonic acid comprises salt formation with the carbonates, oxides or acetates of alkali metals, alkaline earth metals, aluminium and zinc, preferably with ZnO, MgO, Na-acetate. Salt formation is carried out in polar organic solvents, preferably in acetonitrile or acetic acid. The sulfonic acid ester may be obtained from the filtrate by distillation using the procedure described above.

The products obtained by the process according to the invention are valuable organic intermediate products. For example, surface-active substances as well as microbicidally and fungicidally active substances may be obtained by the addition of nucleophilic agents to the double bond.

EXAMPLE 1

Reaction of acrylic acid methyl ester with $SO_3$:

(a) Preparation of a mixture of 2-sulfopropenoic acid methyl ester and 2-methoxy sulfonylpropenoic acid methyl ester:

471 g of liquid sulfur trioxide are stirred at 0° to 10° C. into 506 g of acrylic acid methyl ester stabilised with 2 g of hydroquinone, a gentle stream of an inert gas being simultaneously introduced. After the mixture initially formed has been tempered for 2 hours at 100° C., readily volatile constituents, predominantly unreacted acrylic acid methyl ester and dimethyl sulfate accumulating during the reaction, are distilled off in vacuo. The crude mixture remaining is then introduced into a thin-layer evaporator under the following conditions:

| Temperature of the heating jacket: | 158° C. |
| Pressure adjusted: | 0.5 to 1.0 mbar |
| Throughput: | 1.0 kg/m²h |

The condensate obtained is a substantially colourless oil consisting of 2-sulfopropenoic acid methyl ester and 2-methoxy sulfonyl propenoic acid methyl ester from which the acid precipitates partly in the form of a crystalline phase.

Yield: 622 g (64% by weight, based on the components used, acrylic acid methylester and $SO_3$), The following composition is established by NMR-spectroscopy: 60% by weight of 2-sulfopropenoic acid methyl ester and 40% by weight of 2-methoxy sulfonyl propenoic acid methyl ester.

(b) Isolation of 2-sulfopropenoic acid methyl ester:

The mixture consisting of sulfonic acid and sulfonic acid ester which accumulates during the thin-layer distillation process is stirred with 500 g of benzene, accompanied by brief heating. After cooling, the 2-sulfopropenoic acid methyl ester precipitates in the form of highly pure crystals.

Yield: 200 g (19.5% by weight, based on the components used, acrylic acid methyl ester and $SO_3$)

Melting point: 66° C.

$^1$H-NMR-spectrum (in $d_3$-acetonitrile): δ3.85 (s), 6.85 (d), 6.9 (d), 11.0 (s) ppm (c) Isolation of 2-methoxy sulfonyl propenoic acid methyl ester:

The filtrate remaining after precipitation and separation of the sulfonic acid is concentrated by evaporating off the benzene. The residue is subjected to fractional distillation. The fraction distilling over at 93° C./0.4 mbar consists of 2-methoxy sulfonyl propenoic acid methyl ester.

Yield: 108 g (10.5% by weight, based on the components used, acrylic acid methyl ester and $SO_3$)

Melting point: 25°-30° C.

$^1$H-NMR-spectrum (in $d_3$-acetonitrile): δ3.85 (s), 3.9 (s), 6.9 (d), 7.02 (d) ppm (d) Isolation of the Na-salt of 2-sulfopropenoic acid methyl ester;

66.5 g of the condensate mixture obtained by thin-layer distillation in accordance with (a) are dissolved in 60 g of acetonitrile. 32.8 g of Na-acetate are then introduced in portions with stirring at room temperature. The white solid precipitating is separated off by filtration. After drying, the Na-salt of 2-sulfopropenoic acid methyl ester is left.

Yield: 41.8 g (35 mole percent, based on the acrylic acid methyl ester used)

Melting point: 219° C.

$^1$H-NMR-spectrum (in $D_2O$): δ3.85 (s), 6.65 (d) ppm

The 2-methoxy sulfonyl propenoic acid methyl ester may be obtained from the filtrate by the method described in (c).

EXAMPLE 2 (Comparison Example)

154 g of sulfur trioxide are added dropwise over a period of 40 minutes to 180 g of acrylic acid methyl ester stabilised with 2 g of hydroquinone, an increase in temperature to 55° C. being allowed. The crude mixture accumulating is distilled entirely from a receiver with a short Vigreux column in between in such a way that fractions are separated off under an adjusted pressure of from 0.1 to 1.0 mbar and at temperatures increasing from 60° C. to 180° C. 26 g of a colourless liquid consisting of acrylic acid methyl ester and dimethyl sulfate initially distill over at 60° to 100° C. with vigorous foaming of the mixture initially introduced. Thereafter only a fraction distilling over at 108° to 112° C. can be separated off. Small quantities of a colourless oil identified by spectroscopy as 2-methoxy sulfonyl propenoic acid methyl ester are obtained.

Yield: 27 g (8.1% by weight, based on the components used, methyl acrylate and $SO_3$).

EXAMPLES 3 to 11

The Examples listed in the following Table represent possible variants of the process according to the invention based on changes to important parameters of the process and on the use of different ester components. The procedure is the same as described in Example 1.

| Examples | 3 | 4 | 5 | 6 | 7 | 8 | 9[1] | 10[2] | 11 |
|---|---|---|---|---|---|---|---|---|---|
| Ester component formula II | $R_1$:H $R_2$:$CH_3$ | $R_1$:H $R_2$:$CH_3$ | $R_1$:H $R_2$:$CH_3$ | $R_1$:H $R_2$:$CH_3$ | $R_1$:H $R_2$:$CH_3$ | $R_1$:H $R_2$:$CH_3$ | $R_1$:H $R_2$:$CH_3$ | $R_1$:$CH_3$ $R_2$:$CH_3$ | $R_1$:H $R_2$:$C_2H_5$ |
| Molar ratio ester:$SO_3$ | 1/0.65 | 1/1 | 1/1.6 | 1/1 | 1/1 | 1/1 | 1/1 | 1/1 | 1/1 |
| Process parameters after addition of the $SO_3$ | | | | | | | | | |
| Temperature [°C.] | 100 | 100 | 100 | 100 | 80 | 150 | 100 | 100 | 100 |
| Time [hours] | 1.0 | 0.5 | 1.0 | 5.0 | 1.0 | 3.0 | 2.0 | 2.0 | 2.0 |
| Yield of crude mixture[3] (after thin-layer evaporation) [% by weight] | 34.0 | 63.0 | 47.0 | 59.0 | 46.0 | 64.0 | 61.0 | 45.0 | 40.0 |
| Yield of sulfonic[4] acid (calculated from percentage in the crude mixture) [mole percent] | 32.0 | 57.0 | 55.0 | 44.0 | 41.0 | 50.0 | 57.0 | 38.0 | 34.0 |

[1]$SO_3$ added in the presence of methylene chloride
[2]The sulfonic acid formed during the reaction and also the sulfonic acid ester are present in the form of a cis-/trans-isomer mixture. Separation was not possible.
[3]The values indicated are based on the quantity by weight of the starting components
[4]The yields quoted in mole percent are based on the α,β-unsaturated carboxylic acid esters used.

EXAMPLE 12

Preparation of the magnesium salt of 2-sulfopropenoic acid methyl ester 2 g of magnesium oxide are stirred at room temperature into 16.6 g of 2-sulfopropenoic acid methyl ester dissolved in 30 g of acetonitrile. The white solid obtained after 4 hours is separated off by filtration and washed with acetonitrile, giving a salt corresponding to the following formula:

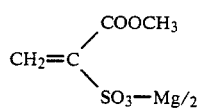

in a yield of 17.7 g (100%, based on the sulfonic acid used).

$^1$H-NMR-spectrum (in $D_2o$): δ3.85 (s), 6.65 (d) ppm

EXAMPLE 13

Preparation of the zinc salt of 2-sulfopropenoic acid methyl ester:

16.6 g of 2-sulfopropenoic acid methyl ester dissolved in 30 g of acetonitrile and 4.1 g of zinc oxide are reacted with stirring at 15° C. The white solid formed after 5 hours is separated off by filtration and washed with acetonitrile, giving a salt corresponding to the following formula:

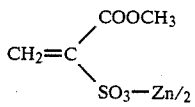

in a yield of 18.8 g (95%, based on the sulfonic acid used).

$^1$H-NMR-spectrum (in $D_2o$): δ3.85 (s), 6.65 (d) ppm

EXAMPLE 14

Reaction of acrylic acid methyl ester, $SO_3$ and dimethyl sulfate.

235 g of liquid sulfur trioxide are stirred at 0° to 10° C. into 253 g of acrylic acid methyl ester stabilised with 2 g of hydroquinone, a gentle stream of an inert gas being simultaneously introduced. The reaction mixture is left to come to room temperature, followed by the rapid addition of 740 g of dimethyl sulfate. After the mixture has been heated for 3 hours to 160° C., 480 g of readily volatile constituents, predominantly dimethyl sulfate, are distilled off in vacuo. The crude mixture is then introduced into a thin-layer evaporator under the following conditions:

| Temperature of the heating jacket: | 145° C. |
|---|---|
| Pressure adjusted: | 0.5 to 1.0 mbar |
| Throughput: | 1.0 kg/m$_2$h |
| A colourless oil is obtained. | |

Yield: 598 g.

A product ratio of 20% of 2-sulfopropenoic acid methyl ester to 80% of 2-methoxy sulfonyl propenoic acid methyl ester is established by NMR-spectroscopy. The product mixture is purified and separated in the same way as described in Example 1.

Yield: 205 g of 2-methoxy sulfonyl propenoic acid methyl ester (42% by weight, based on the components used, methyl acrylate and $SO_3$).

We claim:

1. A process for the production of compounds corresponding to the following formula:

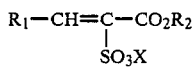

in which $R_1$ represents a hydrogen atom, $R_2$ represents a primary or secondary alkyl group containing from 1 to 4 carbon atoms and X represents a hydrogen atom, a primary or secondary alkyl group containing from 1 to 4 carbon atoms, comprising reacting $\alpha,\beta$-unsaturated carboxylic acid esters corresponding to the following general formula:

in which $R_1$ and $R_2$ are as defined above, with from 0.6 to 1.6 mol. equivalents of sulfur trioxide and, optionally, with from 0.1 to 10 mol. equivalents of an alkylating agent, based in each case on the unsaturated ester, at temperatures in the range from $-10°$ C. to $+25°$ C., heating the reaction mixture to temperatures in the range from 70° to 200° C. then working up by distillation, and optionally separating the components of the distillate.

2. A process as claimed in claim 1, comprising reacting the $\alpha,\beta$-unsaturated carboxylic acid esters for 0.1 to 2.0 hours at $0°+10°$ C. with from 0.8 to 1.2 mol. equivalents of sulfur trioxide.

3. A process as claimed in claim 1, comprising carrying out the reaction in the presence of an organic solvent.

4. A process as claimed in claim 1, wherein
the compound in which X represents hydrogen is separated off from the reaction mixture worked up by distillation either by precipitation with an organic precipitant or by salt formation and the sulfonic acid ester remaining is isolated by distillation.

5. A process as claimed in claim 1, wherein
working up of the reaction mixture by distillation is carried out, optionally after the separation of readily volatile constituents, in a tubular evaporator at temperatures in the range from 100° to 250° C. under a pressure of from 0.05 to 30 mbar, the throughput amounting to between 0.1 and 10 kg/m².h.

6. A process as claimed in claim 1, wherein
acrylic acid methyl ester is used as the $\alpha,\beta$-unsaturated carboxylic acid ester.

7. A process as claimed in claim 1, wherein
from 0.2 to 5 mol. equivalents of a $C_1$-$C_4$-dialkyl sulfate, based on the $\alpha,\beta$-unsaturated carboxylic acid ester, are added to the reaction mixture.

* * * * *